United States Patent [19]
Cho

[11] Patent Number: 5,622,497
[45] Date of Patent: Apr. 22, 1997

[54] TRAY MODELING SYSTEM AND ARTICULATOR FOR PRODUCING A DENTAL MODEL

[76] Inventor: Kyung-Rok Cho, 22720 Woodward Ave., #104, Ferndale, Mich. 48220

[21] Appl. No.: 515,535

[22] Filed: Aug. 15, 1995

[51] Int. Cl.⁶ .............................. A61C 19/00; A61C 9/00; A61C 11/00
[52] U.S. Cl. ................... 433/60; 433/34; 433/37; 433/48
[58] Field of Search .......................... 433/34, 37, 48, 433/60, 214, 213

[56] References Cited

U.S. PATENT DOCUMENTS

| | | | |
|---|---|---|---|
| 3,581,398 | 6/1971 | Thomas | 433/34 |
| 4,200,981 | 5/1980 | Fine | 433/60 |
| 4,439,151 | 3/1984 | Whelan | 433/60 |
| 5,197,874 | 3/1993 | Silva et al. | 433/34 X |
| 5,506,095 | 4/1996 | Callne | 433/60 X |

*Primary Examiner*—Nicholas D. Lucchesi
*Attorney, Agent, or Firm*—Gifford, Krass, Groh, Sprinkle, Patmore, Anderson & Citkowski,P.C.

[57] ABSTRACT

An improved tray system and articulator for use with a replication of a dental patient's teeth taken by a conventional dental impression in the creation of a dental model of the patient's mouth. A first tray and a second tray are provided, each tray having a substantially planar surface upon which a substrate layer of a stone material is applied. An insert is detachably secured to each of the trays and includes an upper keyed portion about which the stone layer bonds. An upper conventional dental impression is secured to the substrate stone layer of the first dental tray and a lower dental impression is secured to the substrate layer of the second dental tray. A reusable articulator includes first and second hinged members which secure to the first and second trays and mount the trays so as to position the teeth replications.

3 Claims, 2 Drawing Sheets

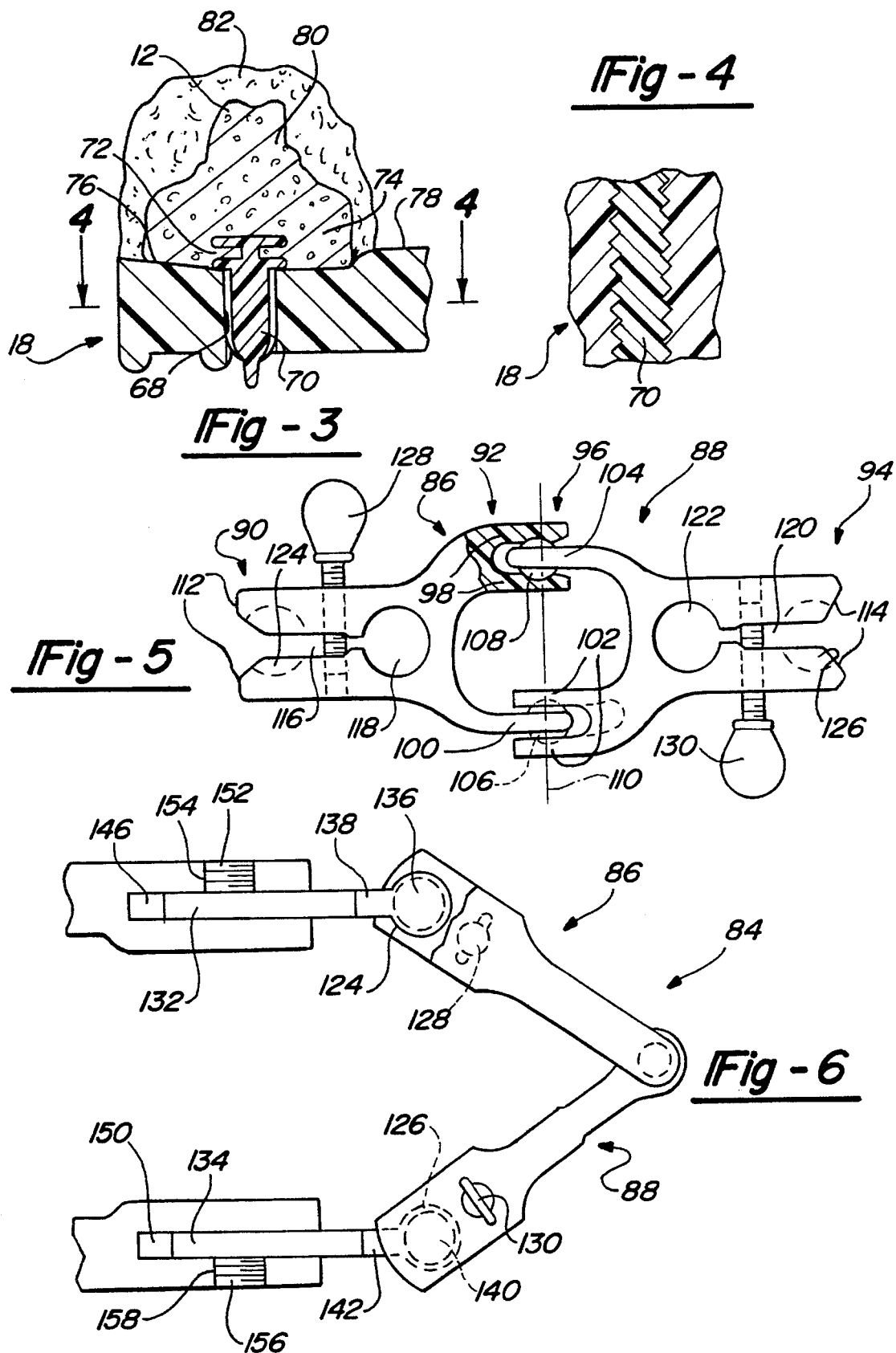

TRAY MODELING SYSTEM AND ARTICULATOR FOR PRODUCING A DENTAL MODEL

BACKGROUND OF THE INVENTION

1. Field of the Invention

The present invention relates generally to modeling devices for mounting teeth replications made from dental impressions to create a dental model of a patient's mouth and, more particularly, to an improved tray modeling system and articulator for producing such a dental model.

2. Description of the Prior Art

Numerous devices are known in the art for creating a working dental model of a patient's upper and lower teeth which are taken from dental impressions at the dentists office. The impression material is typically a malleable compound or a wax-type material which is molded around the patient's upper and lower teeth and gums and which creates a highly accurate negative impression of the teeth and surrounding areas. The impression is then filled with a powderized stone impression material or other appropriate material and is permitted to harden to form a highly accurate replication of the user's teeth. A series of metal dowel pins are inserted into the still hardening stone material which fills the impression at spaced intervals and correspond to the teeth or sections of teeth which are intended to be separated later on. The modeling device is normally engaged by the dowel pins to position and secure the dental impressions of the patient in such a manner so as to provide the dental professional with a highly accurate model of the user's mouth which will make possible the replication of certain of the patient's teeth in the preparation of dentures, crowns and the like.

The Vertex/KV 33 Corporation advertisement brochure teaches a dental impression model in which a powderized stone material similar to that used to create a conventional dental impression of the user's teeth is poured into an open mold. The stone material in the mold is allowed to harden to a certain degree, upon which a release spray coating is applied evenly over the exposed surface. The previously created dental impression is then immediately pressed into the mold base by engaging the dowel pins through the still somewhat malleable mold. The individual teeth or sections of teeth corresponding to the previously placed dowel pins may then be individually cut and separated from the stone base due to the release coating which prevents bonding of the hardening stone in the impression with that from the mold. The release coating allows the separated portions bonded around their respective dowel pins to be easily removed from the stone base and thus enables the specialist to begin preparing his or her model. An articulator, or universal mounting apparatus, is also employed to mount an upper impression model at a desired opposing orientation relative to a corresponding lower impression model to replicate the arrangement of the upper and lower rows of teeth.

While being fairly accurate in providing an accurate dental impression model, the Vertex model suffers from the shortcoming of being very time consuming to produce and necessitating a considerably large amount of stone substrate material, which again requires a considerable amount of setting time. An improvement of the Vertex device is taught by the Dental Ventures of America (DVA) model and die system which, in the place of a standard mold base, provides a predrilled base plate upon which the preformed dental impressions are attached. While the base plate of the DVA system reduces somewhat the time required to assemble the impression into the mold, the required time for producing the initial teeth replications from the impressions and the step of inserting the individual dowel pins into the hardening stone still largely offsets this advantage.

A marked improvement over the conventional impression models is provided by the Nu Logic E-Z Tray Model System which provides a collection of quarter and half trays which are shaped with cavities generally corresponding to the upper and lower impressions of the user's mouth and which define knurled ridges along both inwardly and outwardly facing edges which define the cavity. One or more keyed spine portions are snappingly engaged within groove shaped apertures formed in the bottom center and extending the length of the cavity. The keyed portion of the spine extends upwardly a distance into the cavity and, upon pouring of a quantity of the stone mix into the cavity, is bonded to the stone mix. The spines replace the conventional dowel pins and permit the impression and mold to be directly press fit onto the forming stone mix in the tray.

As further disclosed by the Nu Logic brochure, the model is separated from an overlaying dental impression which is press fit atop the drying stone in the base. The stone case with embedded spine may then be removed as an entire piece from the impression tray. The impression and spine may be cut by an appropriate saw into the desired sections of teeth which can then be remounted onto the tray by aligning the exterior knurled ridges of the stone case with the corresponding inwardly facing knurled ridges on the oppositely facing edges of the tray and then snapping the severed spine portions back in place along the guide slot formed in the bottom of the cavity.

While providing a considerable advantage over conventional dowel pin mounted models, the Nu-Logic device still suffers from the disadvantage of the knurled guiding edges or ridges formed along the inner and outer faces of the stone case being fairly fragile and vulnerable to being chipped or otherwise destroyed due to accident or misuse. Any resultant loss of the integrity of the guiding portions in the stone case would lessen the accuracy of the placement of the impression within the tray. Since there is also nothing aside from the general contour of the spine to prevent it from slipping relative to its axial slot, the opposing knurled portions are the only means of accurately reinserting the dental impressions into the tray.

The prior art further fails to teach an articulator for use with a dental impression model which is easily assembleable and disassembleable, capable of universally positioning and repositioning and locking into place an upper dental impression relative to a lower dental impression, and easily attached and disattached so as to be reusable with different impressions.

SUMMARY OF THE PRESENT INVENTION

The present invention is an improved tray system and articulator for use with a conventional dental impression for creating a dental model of a patient's mouth. The tray system includes in its preferred embodiment a first tray and a second tray. Each tray is generally arch shaped in outline so as to correspond generally to the shape of the dental impression and includes a first substantially planar face and a second substantially planar face separated from the first planar face by a predetermined thickness. The first substantially planar face includes a flat peripheral outer portion and an elevated and central plateau portion which is bounded by the flat outer portion.

A channel shaped recess is formed through the thickness of the tray and extends around the peripheral outer portion. The recess is formed by first and second oppositely facing walls having rows of ridges placed thereon. An insert corresponding to the outline of the recess includes a narrow and elongated body portion having inner and outer rows of ridges which interengage with the rows of ridges on the oppositely facing walls to secure the insert within the recess. A keyed upper portion extends from the body portion and projects above the surface of the peripheral outer portion.

A base layer of stone material is applied over the surface of the peripheral outer portion and surrounds the keyed upper portion of the insert. Another layer of stone material is filled into the conventionally produced impression and, prior to hardening, is press fit onto the layer applied onto the tray so that the layers bond together. The impression and substrate are secured to the tray by the insert and may be detached from the tray by removing the insert from within the channel. The desired teeth or sections of teeth may then be separated by using an appropriate saw or cutting device and then re-attached to the tray by aligning the outwardly facing ridges on the walls of the insert base with the inwardly facing ridges on the walls of the channel.

A novel articulator is also disclosed for positioning and securing a first tray holding a first dental impression in a spaced and opposing fashion relative to a second tray holding a second dental impression in order to recreate a dental model of a patient's mouth. The articulator includes a first member and a second member which are hingedly connected together along a common axis. First and second connecting plates are slidingly inserted and mounted within slots formed in a base of each of the first and second trays and are mounted to the first and second members through universal ball joints which allow the dental impressions on the trays to be oriented as needed to accurately replicate the arrangement of the upper and lower teeth of the patient.

BRIEF DESCRIPTION OF THE DRAWINGS

Reference will now be had to the attached drawing, when read in combination with the following specification, wherein like reference numerals refer to like parts throughout the several views, and in which:

FIG. 3 is a cut-away view taken along line 3—3 of FIG. 2 and showing a cross section of the portion of the tray upon which the stone layer and dental impression are affixed;

FIG. 4 is a cut-away view taken along line 4—4 of FIG. 3 and showing the interengaging ridges of the insert and the channel shaped recess for precisely positioning the severed sections of the dental impression on the tray;

FIG. 5 is a sectional view of the hingedly connecting members of the articulator according to the present invention; and FIG. 6 is a side view of the articulator according to the present invention and showing the manner in which the connecting plates fasten within the upper and lower trays.

DETAILED DESCRIPTION OF THE PREFERRED EMBODIMENT

Figure 1:
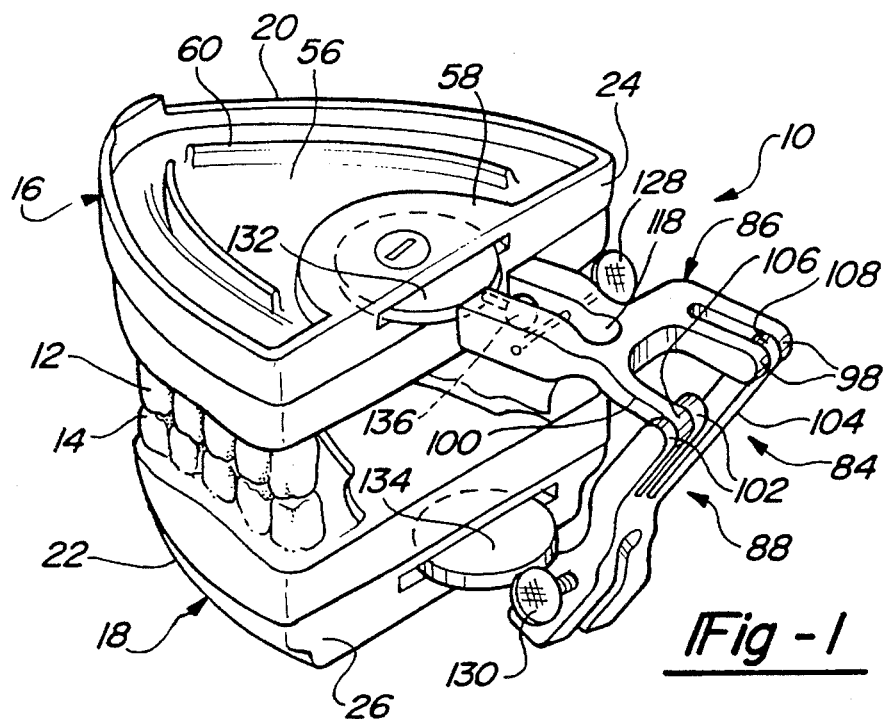
FIG. 1 is an elevational view of the tray system and articulator according to the present invention for mounting upper and lower dental impressions in a dental model of a patient's mouth.
Figure 2:
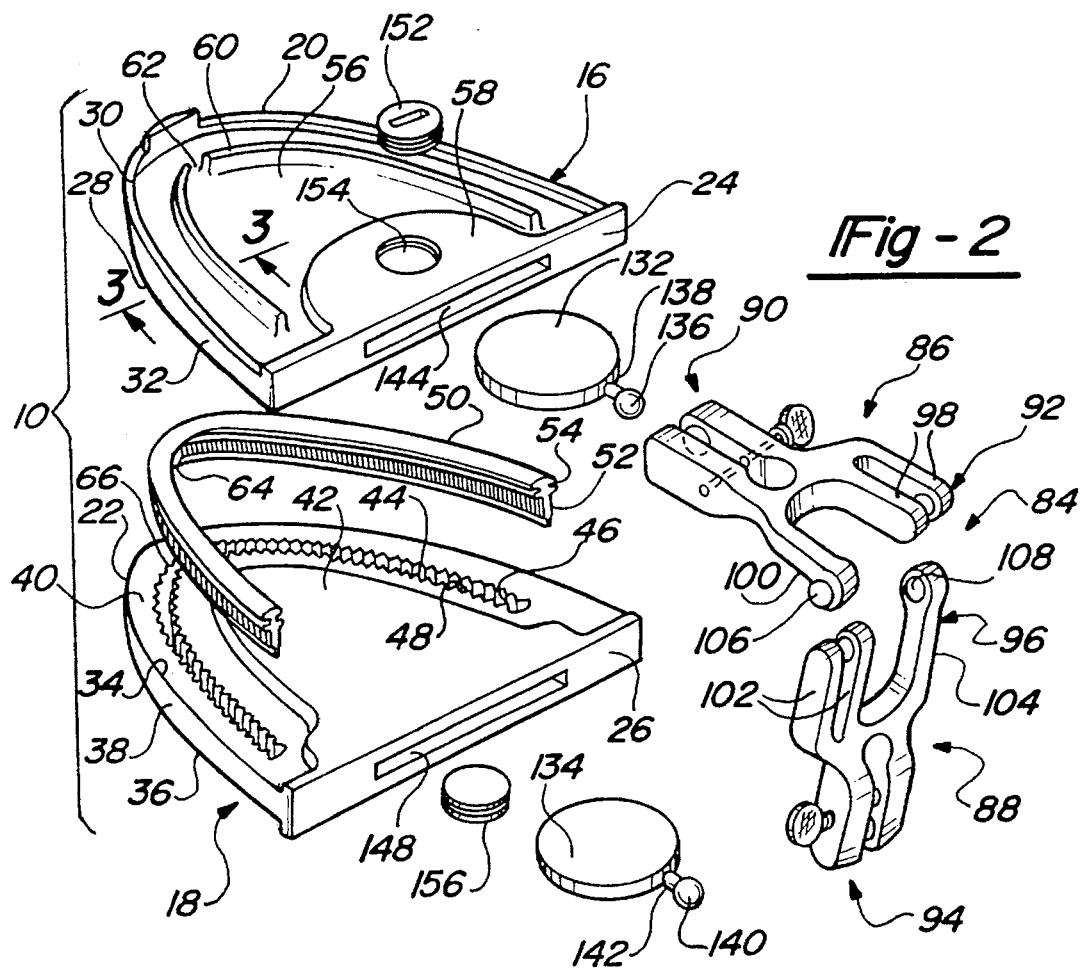
FIG. 2 is a view similar to FIG. 1 and showing an exploded view of the tray system and articulator according to the present invention.

Referring now to FIGS. 1 and 2, an improved tray system and articulator 10 is shown for mounting teeth replications 12 and 14 produced by conventional dental impressions into a dental model of a patient's mouth. As was previously described, the taking of dental impressions at a dentist's office is fairly well known in the art and normally involves fashioning a malleable and highly impressionable material such as a wax compound around the teeth and contours of the patient's mouth. The dental impression is then used by a specialist along with X-rays taken by the dentist to construct a model of the patient's upper and lower teeth in a manner which will be subsequently described.

A first tray 16 and a second tray 18 are provided for mounting, respectively, the teeth replications 12 and 14. Both the first tray 16 and the second tray 18 are constructed of a polymer or like material and form a generally arch shape outline as defined by surfaces 20 and 22. The outline of the trays corresponds generally with the shape of the impressions taken from the patient's mouth. The arch shape outline 20 of the first tray 16 is connected by a straight edge 24 at its base and the arch shape outline 22 of the second tray 18 likewise is connected by a straight edge 26.

Tray 16 includes a first substantially planar face 28 and a second substantially planar face 30 which are separated by a predetermined thickness 32. Likewise, tray 18 includes a first substantially planar face 34 and a second substantially planar face 36 which are separated by a predetermined thickness 38. Referring to tray 18 in FIG. 2, planar face 34 is separated into a flat peripheral outer portion 40 and an elevated and central plateau portion 42 which is bounded by the peripheral outer portion 40. The central plateau portion 42 conforms generally to the outer outline 22 of the tray 18 and is separated from the arched outline 22 by the peripheral outer portion. The plateau portion 42 can be of any height above the flat outer peripheral portion 40, but is preferably between 0.120" and 0.250".

Referring again to tray 18 in FIG. 2, a channel shaped recess 44 is formed through the thickness 38 of the tray 18 in the flat peripheral outer portion 40 and extends around the outer portion 40 between the outer arched outline 22 of the tray 18 and the central plateau portion 42. The channel recess 44 is formed by first 46 and second 48 oppositely facing walls which are spaced apart a predetermined distance and which each include a plurality of ridges formed therealong which extend the length of the recess. An insert 50 corresponds generally to the outline of the channel recess 44 and includes a narrow and elongated body portion 52 and a keyed upper portion 54 extending from the body portion. The body portion 52 includes inner and outer pluralities of ridges which interengage with the pluralities of ridges on the walls 46 and 48 of the channel and which permit the insert to be attached to the channel. The keyed upper portion 54 is substantially H-shaped and projects a distance above the surface of the flat peripheral outer portion 40.

The first planar face 28 of the tray 16 is not visible from FIG. 2, however it is shaped identical in every respect to that of the first planar face 34 of tray 18. Tray 16 in FIG. 2 shows the second planar face 30, identical in all respects to the obscured second planar face 36 of tray 18. The planar faces 30 and 36 represent the undersides of the dental impression trays, and the planar face 30 evident in FIG. 2 includes an outer recessed area 56 surrounding an inner elevated area 58. An elongated body portion of an insert 60, identical to the insert 50, is shown projecting through planar face 30 of the tray 16. The body portion of the insert may be notched at a central point 62 to correspond with an appropriately formed bridge across the width of the channel recess. Referring again to the insert 50 of tray 18, a similar notch 64 is shown for aligning with a bridged portion 66 on the surface of the flat outer peripheral surface 40 for securing the insert in a fixed manner within the channelled recess.

Referring to FIG. 3, a cutaway view shows a cross section of the manner of affixing the replication of the patient's teeth made by the dental impression onto the tray to construct a model according to the present invention. FIG. 3 shows a cross section of the insert 60 engaged within a recess 68 of the tray 16. The insert includes a narrow and elongated body portion 70 and a keyed upper portion 72 extending from the body portion 70. A layer of a stone material 74 is applied onto a flat peripheral outer portion 76 of the first substantially planar face 28 of the tray 16 between the outer edge and the corresponding bordering central plateau portion 78. The stone material 74 is originally provided as a powderized ceramic or like material which is in a powderized form and which is mixed with an appropriate chemical reactant to adopt a flowable state prior to hardening.

Concurrent with the pouring of the layer of stone material onto the tray 18, an additional volume of stone material 80 is poured into a conventional dental impression 82 to create a replication of the patient's teeth. The volumes of stone material 74 and 80 are allowed to set until they reach a semi-hardened state, upon which the impression 82 is press fit atop the stone layer 74 on the tray, upon which the stone layers bond to one another as they complete their hardening cycle. The impression 82 is thereafter removed to reveal the replication produced by the volume of stone 80 mounted atop the substrate layer 74 of material secured to the tray. The substrate layer 74 of stone surrounds and bonds to the keyed upper portion 72 of the insert so that the insert becomes permanently attached to the stone. As is further known in the art, a release spray coating may be applied onto the surfaces of the tray upon which the substrate layer 74 is poured to facilitate the subsequent removal of the stone layer and attached insert from the tray. However, the differences in the properties of the ceramic stone material and the polymer tray usually provide for easy removal of the stone without the need for any additional release agent.

Referring to the cutaway view of FIG. 4, a cross section is shown of the interengaging ridges on the sides of the body portion 70 of the insert 60 corresponding to those placed on the opposing walls making up the channeled recess 68. The interengaging pluralities of ridges between the insert and tray guarantee precise locating of the severed teeth replications once they are reassembled upon the tray. The drawings do not show the actual steps of disengaging the stone and insert from the tray and sawing apart the respective teeth and/or sections of teeth through the insert using a dental hacksaw or the like prior to reassembling the replication on the tray, however these steps are known in the art as described and illustrated in the Nu-Logic promotional brochure previously described. An important advantage of the tray modeling system of the present invention is the provision of the opposing rows of ridges between the side walls of the channelled recesses on the trays and the elongated body portions of the inserts. Since both sets of positioning and interengaging ridges are constructed of heavy duty polymer material, there is little or no possibility of loss of integrity of the ridges with the resultant loss of the ability to successively reattach and relocate the severed teeth portions onto the tray. The Nu-Logic device in contrast utilizes the ridges formed in the outer sides of the stone layer formed vis-a-vis the tray to relocate the teeth impression after fashioning and cutting. As was previously described, the ridges of the stone layer are fairly fragile and any accidental contact or force application will damage the ridges, with an attendant loss of locating support.

Referring again to FIGS. 1 and 2, and also to FIGS. 5 and 6, a novel articulator device 84 is shown for use with the dental model system 10 of the present invention. As is well known in the prior art, articulators are devices for mounting and positioning upper and lower dental replications mounted on their tray or mold bases in opposing fashion in a model of a dental patient's mouth.

The articulator 84 of the present invention includes a first member 86 and a second member 88. Each of the members 86 and 88 is constructed of a durable plastic body having a tray connecting end and a hinge interconnecting end. Specifically, the member 86 has a first end 90 for engaging the tray 16 and a second end 92 for hingedly engaging the member 88. The member 88 likewise has a first end 94 for engaging the tray 18 and a second end 96 for hingedly engaging the member 86 at its second end 92. The second end 92 the member 86 includes a pair of locating guide fingers 98 and a parallel extending receiving finger 100 spaced a distance from the locating guide fingers 98. The second end 96 of the member 88 includes a pair of locating guide fingers 102 and a parallel extending receiving finger 104 spaced a distance from the locating guide fingers 102. The members 86 and 88 are positioned in opposing fashion at their ends 92 and 96 so that the receiving finger 100 of member 86 is snappingly engaged between the locating guide fingers 102 of member 88 and the receiving finger 104 of member 88 is snappingly engaged between the locating guide fingers 98 of member 86. The receiving finger 100 includes an enlarged ball shaped end 106 and the receiving finger 104 includes an enlarged ball shaped end 108 which engage within corresponding hollowed recess portions in the oppositely facing inner walls of the locating guide fingers 98 and 102. The members 86 and 88 are further constructed of a deformable and resilient plastic material which permit the interengaging portions of the hinge members to be snapped together without breaking. The members are thus assembled about a hinged axis 110 shown in FIG. 5 and are capable of pivoting relative to each other about that axis.

Referring specifically again to FIG. 5, the member 86 includes at its other end 90 a pair of spaced apart and inwardly deflectable fingers 112. The member 88 likewise includes at its other end 94 a pair of spaced apart and inwardly deflectable fingers 114. The fingers 112 of member 86 define a slot 116 extending therebetween which terminates in a circular shaped aperture 118 formed in the member at a central portion of its body. The fingers 114 of member 88 likewise define a slot 120 extending therebetween which terminates in a circular shaped aperture 122 formed in the member at a central portion of its body. The oppositely facing surfaces of the fingers 112 and 114 are appropriately shaped to create substantially cylindrical shaped receiving apertures 124 and 126 at the second ends 90 and 94 of the hinge members. A threaded bolt 128 is received in a cross sectional direction through an externally threaded aperture in the body of the member 86 and intersects the slot 116 between the apertures 118 and 124. Another threaded bolt 130 is received in a cross sectional direction through an externally threaded aperture in the body of the member 88 and intersects the slot 120 between the apertures 122 and 126. The shaping of the hinge members with the inner apertures 118 and 122 permit the fingers 112 and 114 to be inwardly deflected upon rotating the bolts 128 and 130 in a tightening direction, the purpose for which will now be described.

Referring again to FIGS. 1, 2 and 6, and specifically to FIG. 2, a connecting plate 132 is provided for attaching the hinge member 86 to the tray 16 and a connecting plate 134 for attaching the hinge member 88 to the tray 18. Both the connecting plates 132 and 134 are substantially disc shaped, with a universal ball joint 136 extending from the plate 132 by a stem 138 and a universal ball joint 140 extending from the plate 134 by a stem 142. The tray 16 is slotted at 144 along its straight edge 24 and forms a cavity 146 which can be seen by the side profile in FIG. 6. The tray 18 is also slotted at 148 along its straight edge 26 and forms a cavity 150 as also seen in FIG. 6. As is further seen from reference to both FIGS. 2 and 6, a threaded disc nut 152 is rotatably engaged within a like threaded aperture 154 formed in the raised portion 58 of the second planar face of tray 16 and a threaded disc nut 156 is likewise rotatably engaged within a like threaded aperture 158 (FIG. 6) formed in a corresponding raised portion on the second planar face of the tray 18. The threaded apertures 154 and 158 communicate with the cavities 146 and 150 such that, upon sliding the connecting plates 132 and 134 into their respective slots 144 and 148, the threaded disc nuts 152 and 156 may be tightened to securably engage the connecting plates within their associated apertures. The disc nuts each include an upper portion which may be grasped by the user's fingers to selectively thread and unthread the discs from the apertures.

Referring again to FIG. 6, the universal ball joint 136 of connecting plate 132 is snappingly engaged in the aperture 124 between the deflectable fingers 112 and the universal ball joint 140 of connecting plate 134 is likewise snappingly engaged in the aperture 126 between the deflectable fingers 114. As can be seen from FIG. 1, the upper mounted dental tray exhibiting teeth 12 may then be positioned in a proper alignment vis-a-vis a corresponding lower mounted dental tray exhibiting teeth 14. The universal ball joints held loosely within their associated apertures may be rotated as needed and the connecting plates may also be slidingly adjusted within their associated cavities in order to accurately position the replicated teeth. The opposing rows of teeth are positioned to correspond with an X-ray taken of the patient's mouth or some other reference to ensure proper orientation of the teeth. Upon achieving satisfactory alignment of the teeth, the threaded disc nuts 152 and 156 and the thumb screws or bolts 128 and 180 are tightened to affix the connecting plates in place and to draw the respective pairs of deflectable fingers against the universal ball joints.

The articulator according to the present invention may be easily dismounted from its associated trays simply be loosening the threaded disc nuts and can be subsequently reused with another set of trays as needed. While the articulator disclosed is a preferred embodiment, it is understood that the system of the present invention could employ other conventional articulators such as those disclosed in the art without deviating from the invention.

The present invention therefore discloses an improved tray modeling system with detachable insert which does away with the need for dowel pins for attaching a teeth replication made from a conventional dental impression to a stone substrate base. The present invention is further an improvement on the Nu-Logic device in that both of the opposing rows of positioning and engaging ridges are formed on durable polymer materials which will not decay or break during subsequent dismounting, cutting and repositioning of the teeth sections. The present invention is further an improvement over other prior art modeling tray devices in that a lesser volume of stone substrate material is needed to provide a base upon with the dental impression replication is mounted.

Having described my invention, additional embodiments will become apparent to those skilled in the art to which it pertains without deviating from the scope of the appended claims.

I claim:

1. An improved tray system and articulator for use with a conventional dental impression for creating a dental model of the patient's mouth, comprising:

at least one tray having a first substantially planar face, a second substantially planar face separated from said first planar face by a predetermined thickness, and at least one side;

said first substantially planar face including a flat peripheral outer portion and an elevated and central plateau portion which is bounded by said flat outer portion;

a channel shaped recess formed through said thickness of said at least one tray and extending around said peripheral outer portion, first and second oppositely facing walls defining said recess and having rows of ridges placed thereon;

at least one insert corresponding in outline to that of said recess, said at least one insert including a narrow and elongated body portion having inner and outer rows of ridges which interengage with said rows of ridges on said oppositely facing walls to secure said insert within said recess, said insert further including a keyed upper portion extending from said body portion and projecting above a surface of said peripheral outer portion;

wherein a base layer of stone is adapted to be applied over said outer portion of said tray and surround said keyed upper portion of said insert;

wherein the dental impression corresponds in shape to said peripheral outer portion and is bonded to said base layer of stone; said at least one tray including a first tray and a second tray, said articulator providing means for positioning and means for securing said first tray holding a first dental impression in a spaced and opposing fashion relative to said second tray holding a second dental impression to recreate a dental model;

said means for positioning and means for securing including a first member having a first end and a second end and a second member having a first end and a second end;

a first connecting plate interconnecting said first end of said first member to said first tray and a second connecting plate interconnecting said first end of said second member to said second tray, said second end of said first member hingedly connecting to said second end of said second member about a common axis;

a first pair of locating guide fingers and a first receiving finger which is spaced a distance from said first pair of guide fingers, said first pair of guide fingers and said first receiving finger extending from a body of said first articulator member toward said second end;

a second pair of locating guide fingers and a second receiving finger which is spaced a distance from said second guide fingers, said second pair of guide fingers and said second receiving finger extending from a body of said second articulator member toward said second end; and said receiving finger of said first articulator member hingedly securing between said pair of locating guide fingers of said second articulator member and said receiving finger of said second articulator member hingedly securing between said pair of locating guide fingers of said first articulator member.

2. The improved tray system and articulator as described in claim 1, further comprising:

a pair of inwardly deflectable fingers extending from said first articulator member toward said first end of said first member and a pair of inwardly deflectable fingers extending from said second articulator member toward said first end of said second member;

a first universal ball joint extending from said first connecting plate and a second universal ball joint extending from said second connecting plate; and said first universal ball joint capable of being snappingly engaged within an appropriately formed aperture between said pair of inwardly deflectable fingers of said first member and said second universal ball joint capable of being snappingly engaged within an appropriately formed aperture between said pair of inwardly deflectable fingers of said second member.

3. An improved tray system and articulator for use with a conventional dental impression for creating a dental model of the patient's mouth, comprising:

at least one tray having a first substantially planar face, a second substantially planar face separated from said first planar face by a predetermined thickness, and at least one side;

said first substantially planar face including a flat peripheral outer portion and an elevated and central plateau portion which is bounded by said flat outer portion;

a channel shaped recess formed through said thickness of said at least one tray and extending around said peripheral outer portion, first and second oppositely facing walls defining said recess and having rows of ridges placed thereon;

at least one insert corresponding in outline to that of said recess, said at least one insert including a narrow and elongated body portion having inner and outer rows of ridges which interengage with said rows of ridges on said oppositely facing walls to secure said insert within said recess, said insert further including a keyed upper portion extending from said body portion and projecting above a surface of said peripheral outer portion;

wherein a base layer of stone is adapted to be applied over said outer portion of said tray and surround said keyed upper portion of said insert;

wherein the dental impression corresponds in shape to said peripheral outer portion and is bonded to said base layer of stone; said at least one tray including a first tray and a second tray, said articulator providing means for positioning and means for securing a first tray holding a first dental impression in a spaced and opposing fashion relative to a second tray holding a second dental impression to recreate a dental model;

said means for positioning and means for securing including a first member having a first end and a second end and a second member having a first end and a second end;

said at least one tray including a first tray and a second tray, a first connecting plate interconnecting said first end of said first member to said first tray and a second connecting plate interconnecting said first end of said second member to said second tray, said second end of said first member hingedly connecting to said second end of said second member about a common axis;

said first tray having a substantially arched surface and an interconnecting straight edged surface and said second tray having a substantially arched surface and an interconnecting straight edged surface;

a first slot formed along said straight edge surface of said first tray and a second slot formed along said straight edge surface of said second tray;

said first slot defining a first cavity in said first tray and said second slot defining a second cavity in said second tray;

said first connecting plate being slidably inserted into said first cavity and said second connecting plate being slidably inserted into said second cavity; and a first threaded disc nut being rotatably engaged through an aperture formed in a second substantially planar surface of said first tray in communication with said first cavity to secure said first connecting plate and a second threaded disc nut being rotatably engaged through an aperture formed in a second substantially planar surface of said second tray in communication with said second cavity to secure said second connecting plate.

* * * * *